US012594219B2

(12) United States Patent (10) Patent No.: US 12,594,219 B2
De Luca et al. (45) Date of Patent: Apr. 7, 2026

(54) ASSISTANCE APPARATUSES FOR CARRYING OUT AN EMERGENCY CARE PROCEDURE, ASSISTANCE SYSTEM FOR SYNCHRONISED CARDIO-PULMONARY RESUSCITATION, AND ASSOCIATED METHOD

(71) Applicant: ARCHEON, Besançon (FR)

(72) Inventors: Alban De Luca, Besançon (FR); Pierre-Edouard Saillard, Besançon (FR)

(73) Assignee: ARCHEON, Besançon (FR)

( * ) Notice: Subject to any disclaimer, the term of this patent is extended or adjusted under 35 U.S.C. 154(b) by 1188 days.

(21) Appl. No.: 17/292,401

(22) PCT Filed: Nov. 8, 2019

(86) PCT No.: PCT/IB2019/059635
§ 371 (c)(1),
(2) Date: May 7, 2021

(87) PCT Pub. No.: WO2020/095276
PCT Pub. Date: May 14, 2020

(65) Prior Publication Data
US 2022/0008285 A1 Jan. 13, 2022

(30) Foreign Application Priority Data
Nov. 9, 2018 (FR) ........................................ 1871428

(51) Int. Cl.
*A61H 31/00* (2006.01)
*A61M 16/00* (2006.01)
*G16H 20/40* (2018.01)

(52) U.S. Cl.
CPC ......... *A61H 31/005* (2013.01); *A61H 31/007* (2013.01); *A61M 16/0003* (2014.02);
(Continued)

(58) Field of Classification Search
CPC .. A61H 31/005; A61H 31/006; A61H 31/007; A61H 31/008; A61H 31/004;
(Continued)

(56) References Cited

U.S. PATENT DOCUMENTS 7,747,319 B2 6/2010 Freeman
7,774,060 B2 8/2010 Westenskow et al.
(Continued)

FOREIGN PATENT DOCUMENTS

CN 1367675 A 9/2002
CN 101061985 A 10/2007
(Continued)

OTHER PUBLICATIONS

International Search Report for International Application No. PCT/IB2019/059635, mailed Feb. 6, 2020, 6 pages with English Translation.
(Continued)

*Primary Examiner* — Joseph D. Boecker
*Assistant Examiner* — Brian T Khong
(74) *Attorney, Agent, or Firm* — TraskBritt

(57) ABSTRACT

An assistance apparatus for carrying out a first emergency care procedure, such as chest compressions or pulmonary ventilation, is configured to cooperate with a second assistance apparatus for carrying out a second emergency care procedure. The assistance apparatus comprises a communication device designed to receive, from the second assistance apparatus, data relating to the second emergency care procedure. The data comprises at least one item of information, a parameter or an instruction. A signal-processing device is configured to process the at least one signal measured according to the received data relating to the second emergency care procedure. An assistance system, comprising a compression assistance apparatus and a ven-
(Continued)

Figure 1:
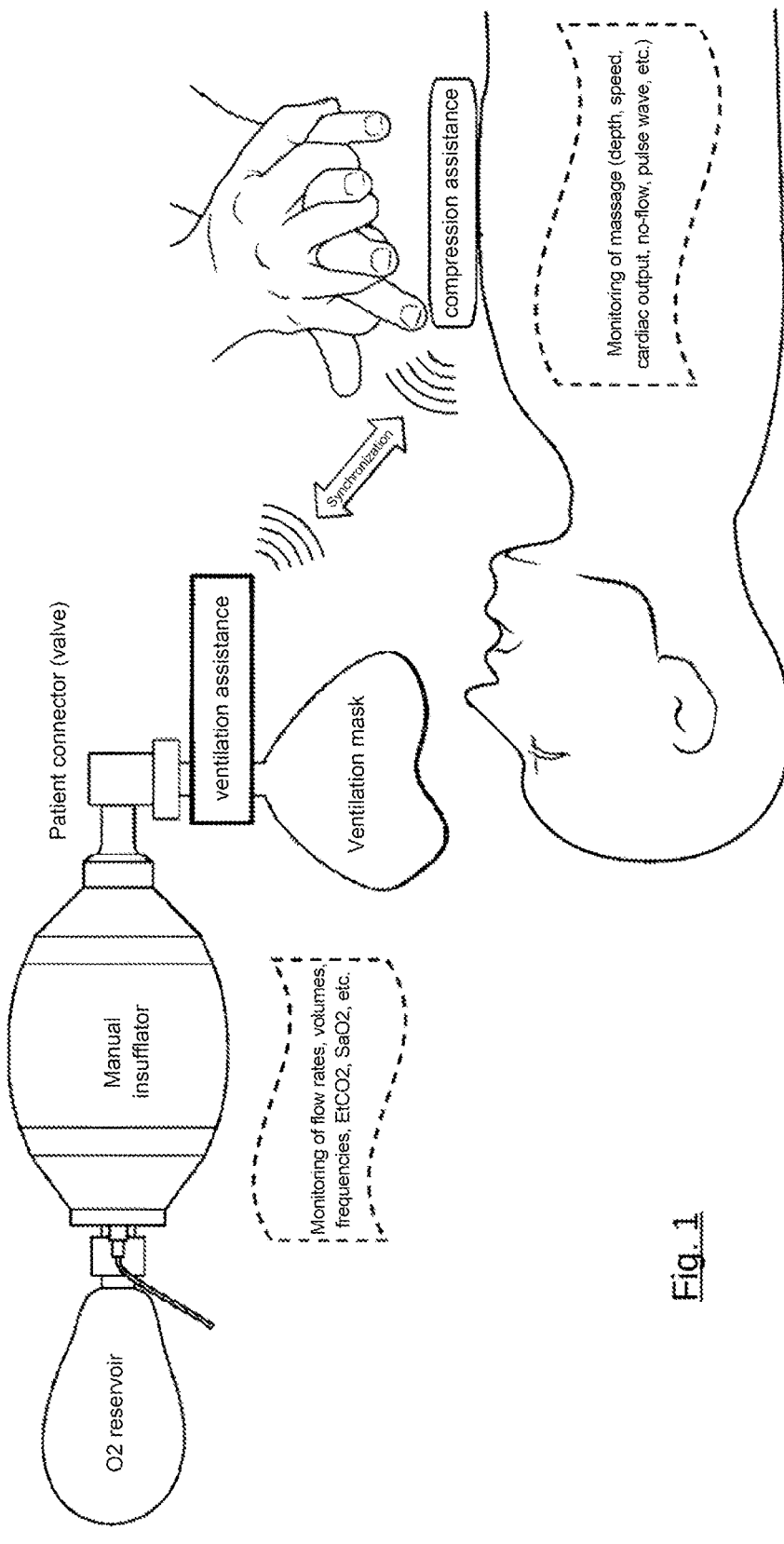

tilation assistance apparatus, and an assistance method associated with the assistance system are also disclosed.

16 Claims, 3 Drawing Sheets

(52) U.S. Cl.
CPC ........ *A61M 16/0084* (2014.02); *G16H 20/40* (2018.01); *A61H 2201/5043* (2013.01); *A61H 2230/207* (2013.01); *A61H 2230/25* (2013.01); *A61H 2230/30* (2013.01); *A61M 2016/0027* (2013.01); *A61M 2230/205* (2013.01); *A61M 2230/432* (2013.01)

(58) Field of Classification Search
CPC ........ A61H 2031/025; A61H 2031/001; A61H 2031/002; A61H 2031/003; A61M 16/0003; A61M 16/0084
See application file for complete search history.

(56) References Cited

U.S. PATENT DOCUMENTS

| | | | |
|---|---|---|---|
| 10,307,099 | B2 | 6/2019 | Kantor et al. |
| 2002/0078954 | A1 | 6/2002 | Davaris et al. |
| 2010/0228166 | A1* | 9/2010 | Centen .................... A61H 31/00 |
| | | | 600/587 |
| 2011/0284004 | A1* | 11/2011 | Silver ............... A61M 16/0084 |
| | | | 128/205.13 |
| 2012/0245442 | A1* | 9/2012 | Ukawa ................. A61H 31/005 |
| | | | 600/324 |
| 2013/0018288 | A1 | 1/2013 | Jaffe |
| 2013/0218057 | A1* | 8/2013 | Jorgenson ............ A61N 1/3925 |
| | | | 601/41 |
| 2013/0324873 | A1 | 12/2013 | Babaeizadeh et al. |
| 2016/0106362 | A1* | 4/2016 | Packer .................... G16H 40/63 |
| | | | 600/301 |
| 2018/0160970 | A1 | 6/2018 | Khoury et al. |
| 2022/0328182 | A1 | 10/2022 | Packer et al. |

FOREIGN PATENT DOCUMENTS

| | | | | |
|---|---|---|---|---|
| CN | 101690694 | A | 4/2010 | |
| CN | 202207285 | U | 5/2012 | |
| CN | 102499875 | A | 6/2012 | |
| CN | 102821733 | A | 12/2012 | |
| CN | 103210391 | A | 7/2013 | |
| CN | 103402426 | A | 11/2013 | |
| CN | 104305994 | A | 1/2015 | |
| CN | 105722551 | A | 6/2016 | |
| CN | 105749390 | A | 7/2016 | |
| CN | 107233204 | A | 10/2017 | |
| EP | 1057451 | B1 | 4/2009 | |
| EP | 2198823 | A1 * | 6/2010 | ............ A61H 31/00 |
| TW | 201601790 | A | 1/2016 | |
| WO | 2008/015623 | A2 | 2/2008 | |
| WO | 2009/037621 | A1 | 3/2009 | |
| WO | 2011/127123 | A2 | 10/2011 | |
| WO | 2012/065167 | A1 | 5/2012 | |
| WO | 2014/078840 | A1 | 5/2014 | |
| WO | 2016/198275 | A1 | 12/2016 | |
| WO | 2017/140280 | A1 | 8/2017 | |

OTHER PUBLICATIONS

International Written Opinion for International Application No. PCT/IB2019/059635, mailed Feb. 6, 2020, 12 pages with English machine translation.
Chinese Office Action and Search Report for Chinese Application No. 201980074044.X, dated Aug. 11, 2023, 19 pages with English machine translation.
Chinese Office Action for Chinese Application No. 201980074044. X, dated May 30, 2024, 22 pages with English machine translation.
Chinese Search Report for Chinese Application No. 201980074044. X, dated Mar. 8, 2024, 1 page English machine translation.
European Communication pursuant to Article 94(3) EPC for European Application No. 19809619, dated Aug. 2, 2024, 13 pages with English machine translation.
Luo et al. Study of Setting of Ventilator Tidal and Airway Pressure Alarm Threshold with Continuous Extra-sternum Heart Compression in Cardiopulmonary Resuscitation, Zhonghua wei Zhong Bing ji jiu yi xue (English: Chin Crit Care Med.), Feb. 2013, vol. 25, Nov. 2, pp. 102-105 (9 pages with English machine translation).
Wang et al., "Common Alarm Analysis and Treatment of Ventilator," Journal of Hebei Medical College for Continuing Education, Feb. 2015, vol. 32, No. 1, pp. 70-75 (12 pages with English machine translation).

\* cited by examiner

Capnography measurement during the chest compressions

Capnography measurement during a ventilation phase

ASSISTANCE APPARATUSES FOR CARRYING OUT AN EMERGENCY CARE PROCEDURE, ASSISTANCE SYSTEM FOR SYNCHRONISED CARDIO-PULMONARY RESUSCITATION, AND ASSOCIATED METHOD

CROSS-REFERENCE, TO RELATED APPLICATIONS

This application is a national phase entry under 35 U.S.C. § 371 of International Patent Application PCT/IB2019/059635, filed Nov. 8, 2019, designating the United States of America and published as International Patent Publication WO 2020/095276 A1 on May 14, 2020, which claims the benefit under Article 8 of the Patent Cooperation Treaty to French Patent Application Serial No. FR1871428, filed Nov. 9, 2018.

TECHNICAL FIELD

The disclosure relates to the field of assistance provided to persons in cardiopulmonary distress and, more precisely in this field, the disclosure relates to assistance apparatuses for carrying out an emergency care procedure and to an assistance system for synchronized cardiopulmonary resuscitation.

BACKGROUND

Cardiac arrest is the primary cause of death worldwide, accounting for nearly 60,000 deaths per annum in France and more than 15 million worldwide. The figures could even double by 2024 with the aging population and the considerable increase in cardiopulmonary diseases. This serious public health problem is all the more worrying since, for almost 20 years now, the survival rate in cardiac arrest has been 5% on average and has not improved despite the considerable efforts that have been made to train and raise awareness in the population of the life-saving maneuvers involved and also to provide automatic defibrillators in public places.

For the past ten years or so, international scientific bodies for cardiac resuscitation, such as the AHA (American Heart Association) and the ERC (European Resuscitation Council), have carried out numerous studies to understand the reasons for this low survival rate and have shown that in most cases the reason lies in the quality of the cardiac resuscitation. Studies show that whatever the level of training and experience of first-response teams, cardiopulmonary resuscitation remains demanding and very difficult to perform, notably under stressful conditions and in the sometimes hostile environments encountered in emergency situations prior to hospital.

Carrying out cardiac resuscitation is a complex process that must involve at least 2 people who have to work in complete synchrony in order to optimize the heart/lung interactions.

On the one hand, the circulation of the blood must be maintained by performing chest compressions with a depth that must be between 5 and 6 cm and at a frequency of 100 to 120 compressions per minute in order to guarantee sufficient cerebral perfusion. At the same time, the patient has to be ventilated at a rate of 8 to 12 ventilations per minute and with a tidal volume of 6-7 ml/kg in order to generate intermittent positive pressure in the lungs, prevent collapse of the bronchioles and of the pulmonary vascular system, and thus guarantee sufficient systemic oxygenation.

If ventilation of the patient is necessary for survival, it generates at the same time intrathoracic pressures, which, if they are too high, reduce venous return, preventing the heart from filling normally and impacting on the effectiveness of cardiac massage. This affects cerebral perfusion and leads to a marked decrease in the patient's chances of survival. Conversely, insufficient ventilation does not permit good elimination of CO2 or a sufficient oxygenation rate to keep the brain alive. The right balance of ventilation parameters is therefore essential to maintain the patient's chances of survival and to limit neurological sequelae. Several recent patents have described inventions making it possible to better control the ventilation parameters during cardiac resuscitation. Patent applications WO201478840 and WO2016198275 disclose devices permitting measurement of and feedback on ventilation parameters such as ventilation frequencies, tidal volumes and pulmonary pressures notably. However, it has been observed in practice that some feedback is imprecise, in particular during the performance of chest compressions.

As regards cardiac massage, studies show that the chances of a return to spontaneous circulation are affected by the quality of the chest compressions, which, if performed too slowly or too quickly, do not allow an adequate blood flow to be generated. Likewise, the depth of the compressions influences the amount of blood ejected at each compression and must be controlled in order to guarantee good cerebral perfusion. However, the most decisive factor influencing the patient's chances of survival remains the reduction of the "no-flow" time, that is to say the period of time during which the chest compressions are interrupted, for auscultation in order to intubate the patient and perform invasive ventilation, or most of the time in order to have the necessary time for patient ventilation.

Ventilation is carried out most of the time using a face mask, which must be perfectly positioned and firmly held on the patient's face in order to avoid leaks and to allow effective ventilation. This type of ventilation is the most widely used because it can be practiced by all types of medical and paramedical personnel and does not require specific training as in the case of tracheal intubation. However, it cannot be performed simultaneously with the cardiac massage because in this case it is very difficult to control the leaks, and the air travels in an uncontrolled manner toward the stomach, which generally leads to regurgitation and can cause aspiration of secretions in the patient's airways.

Controlling the quality of chest compressions and reducing the no-flow time are a critical aspect of resuscitation, and several patents have focused on the control of chest compressions. The patents and patent applications EP1057451, WO2009037621 and WO2008015623 all describe systems based on motion sensors, accelerometers and/or pressure sensors, which will make it possible to determine, in particular, the frequency and the depth of chest compressions in order to compare them with reference values, thus making it possible to indicate to the rescuer whether the massage is correctly performed or not. However, here too, it has been observed in practice that some feedback is imprecise, in particular during the performance of ventilation.

In recent years, assistance apparatuses dedicated either to control of ventilation parameters or to control of chest compressions have therefore been developed in order to guide rescuers in the practice of cardiopulmonary resuscitation. These devices, used separately or jointly, have not yet proven to bring any real benefit in the care of the patient or to have any impact on the survival rate or on the return to spontaneous blood circulation.

The effectiveness of cardiopulmonary resuscitation is in fact based on a precarious balance between a set of maneuvers that require an advanced level of cooperation between the various persons involved. The massage and ventilation instructions and the decision-making cannot result only from the observation of a single parameter and must therefore be based on a more complex interpretation of the compression and ventilation parameters depending on the situation encountered and on the characteristics of the patient in order to allow precise feedback to the first response team and thus guarantee optimal resuscitation in all circumstances.

Several recent publications therefore describe systems making it possible to receive data from different sensors and to control variables associated with ventilation and also variables associated with cardiac massage. The patent applications WO2011127123 and W0201265167 disclose sensors communicating by wireless link to a monitoring device, making it possible to display and group the information on ventilation and cardiac massage on the same screen.

However, in most cases the display of multiple items of information on the same screen makes the interpretation of the variables difficult for the rescuer, all the more so for personnel who have followed a relatively short course of training and who have little experience in the management of life-threatening emergencies.

BRIEF SUMMARY

The disclosure proposes novel assistance apparatuses for carrying out an emergency care procedure, in particular cardiopulmonary resuscitation, the apparatuses being without at least one of the above-described disadvantages of the known devices.

More particularly, the disclosure relates to an assistance apparatus for carrying out a first emergency care procedure such as chest compressions on a thoracic cage of a patient or pulmonary ventilation, the assistance apparatus being configured to cooperate with a second assistance apparatus for carrying out a second emergency care procedure, the assistance apparatus comprising:

a measuring device configured to measure at least one variable representative of the first care procedure carried out and to produce at least one measurement signal, and a signal-processing device configured to determine, from the at least one measured signal, a value of at least one quality parameter of the first care procedure carried out, the assistance apparatus, according to the disclosure, being characterized in that it also comprises a communication device configured to receive, from the second assistance apparatus, data relating to the second emergency care procedure, the data comprising at least one item of information, a parameter or an instruction, and in that the signal-processing device is configured to process the at least one measured signal according to the received data relating to the second emergency care procedure.

Thus, in an assistance apparatus according to the disclosure, on the basis of a measured signal, the signal-processing device determines at least one quality parameter of the care procedure carried out, taking into account data received relating to a second emergency care procedure. In other words, in order to determine the value of the quality parameter, the processing device processes the measured signal in a manner that takes into account, in real time, data relating to the second emergency care procedure. For example, if the data of the second emergency care procedure change as the procedure is carried out, the processing device will change the processing applied to the measured signal. The value of the obtained quality parameters is thus more precise and/or more relevant to the rescuer. This makes it possible to determine the quality of the emergency care performed by taking into consideration in real time all of the emergency care procedures provided to the patient simultaneously. This also al lows the rescuer using the assistance apparatus to perform a more efficient emergency care procedure.

In the above passages, and more generally throughout the description and the claims of the present patent application, the term "variable" is used to mean a physical quantity measured or measurable by the measuring device. For its part, the term "parameter" is used to mean a parameter that relates to the quality of the associated care procedure, the parameter being derived from the measured signal, the parameter being determined by the signal-processing device, as will be seen from examples below.

An assistance apparatus according to the disclosure can also comprise an alert device configured to produce an alert signal if the determined value of the at least one quality parameter is outside of a setpoint range, the setpoint range comprising expected values of the quality parameter, of which setpoint range at least one of the limits is determined according to the data received relating to the second emergency care procedure.

The alert signal allows the rescuer to detect and quickly correct a care procedure that is not appropriate. The fact that at least one of the limits of the setpoint range can be adjusted depending on the second emergency care procedure in progress makes it possible, in particular, to take account of any disturbances caused to the measured signal by the parallel performance of the second emergency care procedure, as will be seen farther below.

According to one embodiment, the alert device can be configured to fix a lower limit of the setpoint range for a quality parameter at a first value, if the communication device receives an information item of the type "other care procedure in progress," and otherwise at a second value. By adjusting, for a given quality parameter, a limit of the associated setpoint range by taking account of data relating to a second care procedure, the alert device avoids generating alert signals that would be generated by the simple presence of disturbances caused to the measured signal by the parallel performance of a second care procedure but that are not representative of the actual quality of the first care procedure performed, as will be seen more clearly below in examples.

In an assistance apparatus according to the disclosure, the measuring device can comprise at least one sensor for measuring the variable representative of the first care procedure, and a control circuit of the measurement sensor configured to calibrate the measurement sensor if the communication device receives an information item of the type "no other care procedure in progress." Thus, by taking account of data supplied by another assistance apparatus capable of disturbing the measuring device, the calibration of the measurement sensor(s) is more precise and more accurate and then makes it possible to obtain, during the measurements, signals that are closer to the reality of the patient.

An assistance apparatus according to the disclosure can also comprise a display device configured to display the determined value of the at least one quality parameter. The display of one or more quality parameters relating to the quality of the care procedure performed allows the rescuers to better adjust their efforts, their maneuvers, in order to carry out an optimal care procedure.

According to one embodiment, the display device can also be configured to display an alert signal. The display of a possible alert signal associated with a quality parameter allows the rescuer to react as soon as possible in order to correct their efforts and their maneuvers for a more effective care procedure.

Equally, according to one embodiment, the display device can also be configured to display instructions for carrying out the first emergency care procedure, the instructions comprising, in particular, an expected value of the at least one quality parameter of the first emergency care procedure, the expected value depending on the received data relating to the second emergency care procedure. The display of precise instructions, taking into account data supplied by another assistance apparatus associated with another emergency care procedure in progress, allows the rescuer to coordinate their maneuvers optimally with the maneuvers of the rescuer who is performing the other emergency procedure.

In an assistance apparatus again, the communication device can also be configured to receive from a rescuer a choice of assistance protocol to be executed, the protocol comprising, in particular, the first emergency care procedure and the second emergency care procedure, and the display device can also be configured to display suitable instructions for the performance of the first emergency care procedure, the instructions being a function of the received data relating to the second emergency care procedure.

This allows a third party (who may be one of the rescuers working with one of the assistance apparatuses) to choose the best overall assistance protocol to follow for an optimally coordinated cardiopulmonary resuscitation, for example according to the general condition of the patient and of their environment, the display device then displaying only the instructions that relate to the assistance procedure associated with it, while taking into account the data received from the other of the assistance apparatuses, the data being, for example, instructions displayed by the display device of the other assistance apparatus and/or quality parameters determined by the processing device of the other assistance apparatus.

According to one embodiment, the assistance apparatus is of the type for providing assistance in performing compressions on a thoracic cage of a patient, the apparatus being called a compression assistance apparatus, in which apparatus:

the variable representative of the compressions is chosen from a set of compression variables comprising, in particular, a pressure exerted on the thoracic cage of the patient and an acceleration relative to a movement of the thoracic cage of the patient, and the at least one quality parameter of the compressions is chosen from a set of compression parameters comprising, in particular, a number of compressions performed, a frequency of the compressions performed, and an amplitude of the compressions performed.

According to another embodiment, the assistance apparatus is of the type for providing assistance in performing ventilation on a patient, the apparatus being called a ventilation assistance apparatus, the assistance apparatus being configured to cooperate with a ventilation mask coupled to a ventilation device for supplying respiratory gas, in which ventilation assistance apparatus:

the variable representative of the ventilation is a variable chosen from a set of ventilation variables comprising, in particular, a flow rate of inspired gas, a flow rate of expired gas, a pressure of the inspired gas, and a pressure of the expired gas, and the at least one ventilation quality parameter is chosen from a set of ventilation parameters comprising, in particular, a ventilation frequency, a volume of inspired air, a volume of expired air, a tidal volume or effective volume, a percentage of leaks, an insufflation pressure, an end-expiratory pressure, an insufflation time, and an expiration time.

The disclosure also relates to an assistance system for cardiopulmonary resuscitation comprising a compression assistance apparatus and a ventilation assistance apparatus as are described above, the compression assistance apparatus and the ventilation assistance apparatus being intended to be used by at least two separate rescuers, the system being characterized in that, in at least one of the assistance apparatuses, the data processing device is configured to process the at least one measured signal according to the data received from the other of the assistance apparatuses.

Thus, in a system according to the disclosure, each assistance apparatus retains its autonomy in the sense that it itself processes the signal(s) that it measures and can itself display quality parameters and/or alert signals that it produces, while taking into account data received from the other assistance apparatus in order to improve the quality and efficiency of processing of the measured signals.

Finally, the disclosure relates to a method for displaying a combination of emergency care procedures, the method being implemented with the aid of an assistance system as described above, the method comprising the following steps:

in at least one of the assistance apparatuses, the communication device receives an assistance protocol from one of the rescuers and transmits the assistance protocol to the communication device of the other of the assistance apparatuses, in the compression assistance apparatus, the display device displays instructions for carrying out the compression procedure of the assistance protocol, the instructions depending on the compression procedure and depending on the data received from the ventilation assistance apparatus, and in the ventilation assistance apparatus, the display device displays instructions for carrying out the ventilation procedure, the instructions depending on the ventilation procedure and depending on the data received from the compression assistance apparatus.

Examples of implementation of the method are set out in further detail below.

The assistance system according to the disclosure and the associated method thus make it possible to provide the rescuers/first responders with the right level of information necessary for correct performance of the maneuvers and for good decision-making, without in so doing diverting the attention of the rescuers or affecting their concentration by supplying information that is not directly addressed to them or that is of no real interest as regards the urgent task entrusted to them. The two assistance apparatuses can thus be used by two different rescuers or two different teams of rescuers without the need for direct contact to synchronize their respective activities.

In summary, the disclosure not only aims to collect information related to the quality of the emergency care procedures such as chest compressions and ventilations, but also to be able to interpret the information in order to analyze the situation as a whole and thus to give rescuers the right level of information necessary for the proper performance of maneuvers and for good decision-making, without in so doing diverting the attention of the rescuers or affecting their concentration by supplying information that is not directly addressed to them or that is of no real interest as regards the task entrusted to them.

Additional features of the assistance apparatuses and of the assistance system according to the disclosure are mentioned in the dependent claims and in the detailed description that follows; these additional features can be taken alone or in all possible combinations.

BRIEF DESCRIPTIONS OF THE DRAWINGS

Figure 2:
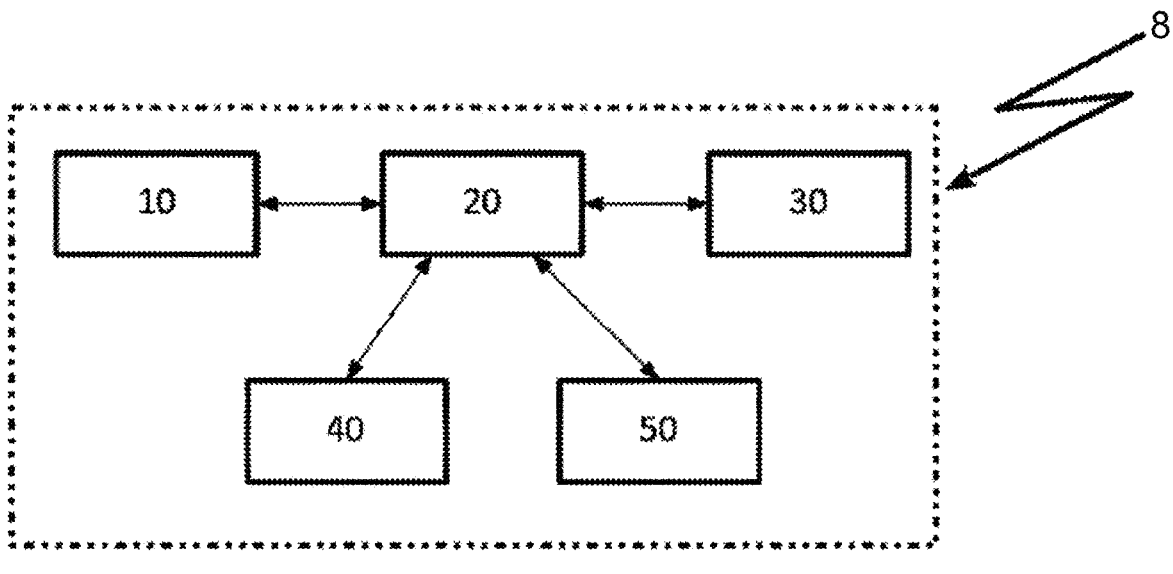
Figure 3:
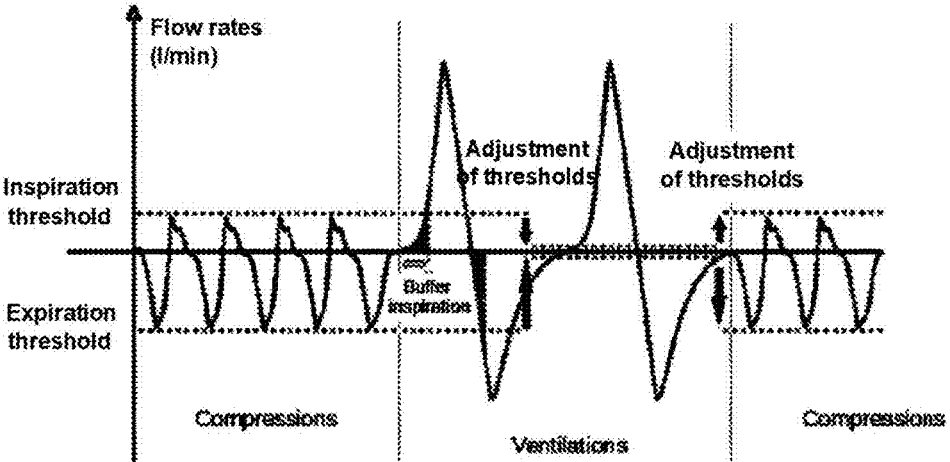
Figures 4A, 4B:
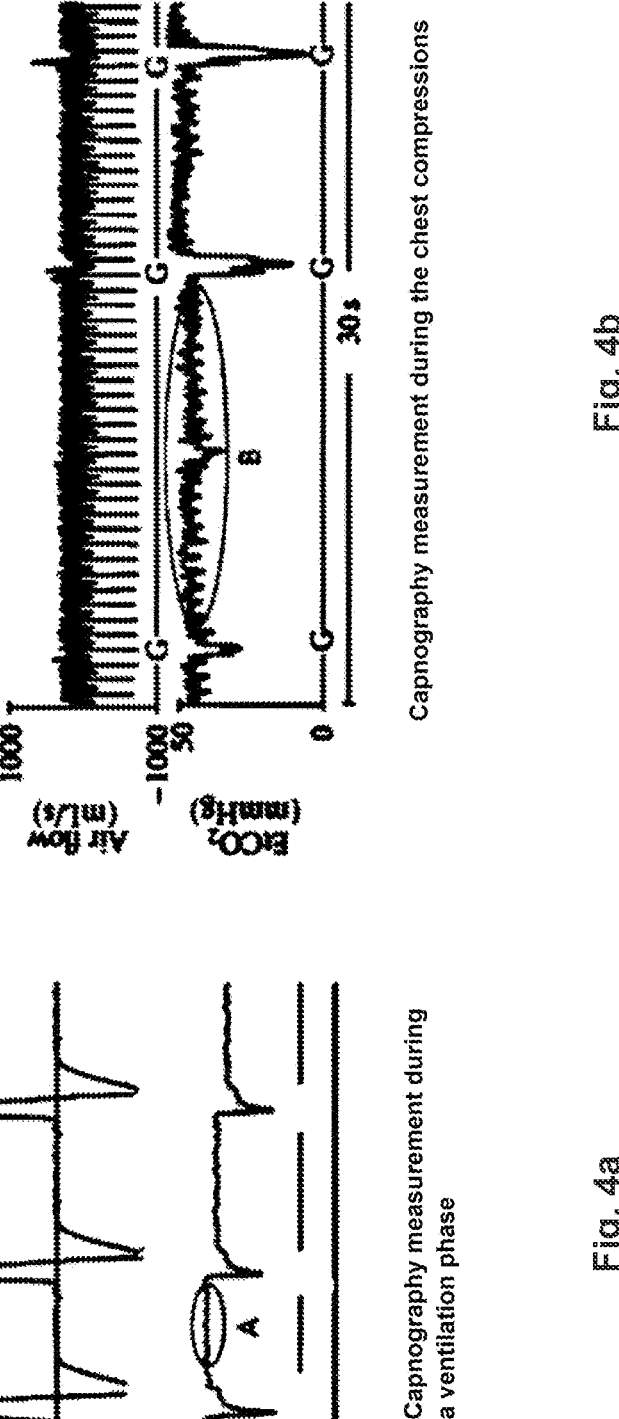

The disclosure will be better understood, and other features and advantages of the disclosure will become clear, on reading the following description of examples of implementation of the disclosure. These examples are given without limitation. The description should be read in conjunction with the accompanying drawings in which:

FIG. 1 is a diagram of an assistance system according to embodiments of the disclosure, put into situation, FIG. 2 is a block diagram of an assistance apparatus according to embodiments of the disclosure, FIG. 3 is a graph showing the change of a respiratory flow rate as a function of time, FIG. 4*a* is a graph showing the change of capnography as a function of time, presenting a change in a quantity of $CO_2$ present in expired air during performance of ventilation, and FIG. 4*b* is a graph showing the change of capnography as a function of time, presenting the change in the same variable as FIG. 4*a* during performance of chest compressions.

DETAILED DESCRIPTION

As stated previously, the disclosure relates to assistance apparatuses 8 (FIG. 2) for carrying out an emergency care procedure, such as performing compressions (apparatus that will hereinafter be called a "compression assistance apparatus" 8) on a thoracic cage or performing pulmonary ventilation (apparatus that will hereinafter be called "ventilation assistance apparatus" 8). Each assistance apparatus 8 is configured to carry out a first emergency care procedure and to cooperate with another assistance apparatus 8 for carrying out a second emergency care procedure. The disclosure also relates to an assistance system using two assistance apparatuses 8 for carrying out optimal cardiopulmonary resuscitation, and to an associated assistance method.

Each assistance apparatus 8 (FIG. 2) according to the disclosure comprises a measuring device 10 and a signal-processing device 20. The measuring device 10 is configured to measure at least one variable representative of the first care procedure carried out and to produce at least one measurement signal. The signal-processing device 20 is configured to determine, from the at least one measured signal, a value of at least one quality parameter of the first care procedure carried out.

According to embodiments of the disclosure, an assistance apparatus 8 is characterized in that it also comprises a communication device 30 configured to receive, from the second assistance apparatus (e.g., another assistance apparatus 8), data relating to the second emergency care procedure, the data comprising at least one item of information, one parameter or one instruction, and in that the signal-processing device 20 is configured to process the at least one measured signal as a function of the received data relating to the second emergency care procedure.

The word "data" must be understood here in the broad sense: the data received can be information items, instructions, parameter values, etc. The expression "emergency care procedure" must be understood here as a sequence of care steps, at least one step, to be carried out by a rescuer. A care instruction is a step of a care procedure that defines an action to be performed by a rescuer, for example "perform C1 compressions at a frequency C2 and depth C3" or "perform V1 ventilations of a volume V2." Finally, a "care protocol" comprises an emergency care procedure or a combination of at least two emergency care procedures.

An assistance apparatus 8 can take the physical form of a small housing having dimensions of the order of a few centimeters in order to be easily transportable, so that it can be positioned, when in use, in a place easily accessible to the eye of the rescuer attending to the patient, but does not interfere with their movements. Preferably, the assistance apparatus 8 comprises an electrical energy accumulator, in order to be autonomous in terms of energy, and communicates with the other assistance apparatus (e.g., another assistance apparatus 8) by a wireless link such as a Bluetooth connection.

According to embodiments of the compression assistance apparatus 8, the housing can be coupled to a strap to be attached to the wrist of the rescuer, or else coupled to an adhesive patch to be stuck on an arm or a shoulder or the chest (cf. FIG. 1) of the patient, or more generally on any suitable support in the immediate vicinity of the rescuer. As a variant, the housing of the compression assistance apparatus 8 can be fixed in the immediate vicinity of the rescuer and a measurement sensor of the measuring device 10 is moved outside the housing in order to be fixed on the patient's chest. For its part, the ventilation assistance apparatus 8 is configured to cooperate with a ventilation mask coupled to a ventilation device for supplying a respiratory gas, the mask being configured to allow the gas to be insufflated into the lungs of a patient. According to a practical embodiment, the housing of the assistance apparatus 8 can be connected between the supply tube and the ventilation mask.

In each assistance apparatus 8, the measuring device 10 can be configured to measure one or more variables representative of the care procedure carried out and to produce one or more corresponding measured signals. Similarly, in each assistance apparatus 8, the signal-processing device 20 can be configured to determine, from the measured signals, a value for one or more quality parameters of the care procedure carried out.

According to one embodiment, for the compression assistance apparatus 8,

According to one embodiment, for the compression assistance apparatus, the variable representative of the compressions is chosen from a set of compression variables comprising, in particular, a pressure exerted on the thoracic cage of the patient and an acceleration relative to a movement of the thoracic cage of the patient, and the at least one compression quality parameter is chosen from a set of compression parameters comprising, in particular, a number of compressions performed, a frequency of the compressions performed, and an amplitude of the compressions performed.

In a practical example, the measuring device 10 comprises a pressure sensor or an accelerometer, and the processing device executes algorithms otherwise known, which make it possible to calculate the number of compressions performed, the frequency and the depth of the compressions performed as a function of the change over time of the pressure exerted on the patient's chest or of the acceleration resulting in a displacement of the thoracic cage. In addition, optionally, the set of compression variables also comprises an arterial pressure and a venous pressure, and in which the set of compression parameters also comprises parameters relating to a quality of the patient's hemodynamics, in particular a cerebral perfusion, a coronary perfusion, a blood flow rate, a blood pressure.

According to one embodiment, for the ventilation assistance apparatus 8, the variable representative of the ventilation is a variable chosen from a set of ventilation variables comprising, in particular, a flow rate of inspired gas, a flow rate of expired gas, a pressure of the inspired gas, and pressure of the expired gas, and the at least one ventilation quality parameter is chosen from a set of ventilation parameters comprising, in particular, a ventilation frequency, a volume of inspired air, a volume of expired air, a tidal volume or effective volume, a percentage of leaks, an insufflation pressure, an end-expiratory pressure, an insufflation time, and an expiration time. In addition, optionally, the set of ventilation variables also comprises a variable representative of an oxygenation of the patient, and in which the set of ventilation parameters also comprises parameters relating to a quality of the oxygenation of the patient, in particular a quantity of $CO_2$ present in the expired gas (EtCO2) and a quantity of oxygen in the blood (SaO2).

According to one embodiment, in an assistance apparatus 8 according to the disclosure, the signal-processing device 20 is configured to determine the value of the at least one quality parameter according to a first determination method, if the communication device 30 receives an information item of the type "other care procedure in progress" and, otherwise, according to a second determination method different from the first determination method. The overall functioning of the signal-processing device 20 is thus modified depending on a received information item relating to another care procedure followed by another assistance apparatus 8.

The first determination method and the second determination method each comprise an algorithm and an initial parameterization, and in which the second determination method comprises:

an algorithm different from the algorithm of the first determination method, or an initial parameterization different from the initial parameterization of the first determination method.

Here, algorithm is understood as a mathematical calculation method otherwise known, making it possible to calculate a parameter derived from a measured signal. For example, depending on the parameters that are to be determined from the measured signal changing over time, an algorithm can be a calculation of a mean value, of a minimum value or of a maximum value over a moving time window, or else an integration of the signal between two values of the signal, etc.

In a variant, the first determination method and the second determination method are distinguished by different signal-processing algorithms (that is to say algorithms comprising at least one different step). In a practical embodiment example, the variable measured is a change over time in the quantity of $CO_2$ present in the expired air (capnography). The capnography (or EtCO2) is a reflection of the elimination of $CO_2$, which gives an indication of the quality of the gas exchanges and therefore of the efficiency of the cardio-pulmonary resuscitation. FIG. 4*a* presents a change in the quantity of $CO_2$ present in the expired air during the performance of ventilation, and FIG. 4*b* presents the change in this same variable during the performance of chest compressions. As can be seen in these FIG. 4*a* and FIG. 4*b*, the change in the quantity of $CO_2$ present in the expired air is greatly impacted by the presence of chest compressions, which makes its interpretation very complex. The fact of using a first specific algorithm to determine, from the measured signal, a parameter representative of the capnography when compressions are in progress, and a second algorithm if they are not, makes it possible to obtain a value of the quality parameter that is more precise and more relevant, in particular when compressions are in progress. The second algorithm, in the absence of compressions, is based, for example, on the identification of a tele-expiratory stage (FIG. 4*a*, stage A at the end of the patient's expiration phase). The first algorithm, in the presence of compressions, is based, for example, on the calculation of a mean value of the parameter representative of EtCO2, over a moving window of 2 to 5 seconds (FIG. 4*b*, stage B).

In another practical example, the variable measured as a function of time is a depth of the patient's chest; to extract from this variable a number of compressions, a first algorithm is used when ventilations are in progress, and a second algorithm when they are not.

In another variant, the first determination method and the second determination method use the same signal-processing algorithm but are distinguished from each other by different initial parameterizations, as is the case in the example detailed below.

During the performance of compressions, passive ventilations of the patient are established, which generate inspirations/expirations of gas of a volume lower than the dead space of the airways, hence inspirations/expirations with no effect on the patient. The disclosure takes into account the volumes of these passive inspirations/expirations in order to determine more precisely, in the following manner, the volume of gas actually inspired or expired by the patient.

In a known manner, the detection of the active ventilations and the calculation of the volumes inspired or expired during an active ventilation are based on measuring the change over time in the flow rate of gas circulating through the ventilation device. An inspiration phase is detected when the flow rate is positive and goes above a high threshold. An expiration phase is detected when the flow rate is negative and falls below a low threshold. The inspired or expired volumes of gas are then calculated by integrating the flow rate curve (curve shown in FIG. 3). For this, flow rate measurements are carried out at regular sampling intervals and, as soon as an inspiration or expiration phase is detected, the flow rate signal is integrated over the period of time determined by the exceeding of the high and low thresholds. To take account of a calculation time and a latency time between the real instant of the start of an inspiration and the instant of the detection of the inspiration, or between the real instant of the start of an expiration and the instant of detection of the expiration, a buffer (or buffer memory) stores a predetermined number of samples throughout the measurement. During the compressions, it is preferable to set detection thresholds high enough not to detect the gas flows generated by the passive ventilations. By contrast, during the active ventilation phases, it is preferable to have detection thresholds as low as possible in order to detect as quickly as possible the change-over from an inspiration phase to an expiration phase or the change-over from an expiration phase to an inspiration phase and thereby determine as precise as possible a volume of inspired or expired gas. The choice of the detection thresholds is usually a compromise between an ideal low threshold and an ideal high threshold. This results in volumes of inspired or expired gas of which the value is sometimes erroneous to within a few tens of percent.

To overcome this difficulty, the disclosure proposes using the same signal-processing algorithm but with initial parameterizations that are different or that change over time:

if compressions are in progress, an initial parameterization comprising high detection thresholds and a large buffer, and otherwise, an initial parameterization comprising low detection thresholds (lower than the high detection thresholds) and a small buffer (i.e., smaller than the size of the large buffer).

During the compressions, high thresholds make it possible to avoid detecting passive ventilations, and a large buffer makes it possible to ensure that, during a transition to an active inspiration or expiration phase (start of active ventilation), the samples measured between the actual start time of the active inspiration (or expiration) phase and the time of detection of the active inspiration (or expiration) phase have been memorized and can be taken into account in the calculation of the inspired (or expired) gas volume. By contrast, aside from the compressions, low detection thresholds make it possible to detect as quickly as possible the start or the end of an active inspiration or expiration phase in order to determine with greater precision the volume of inspired or expired gas; and the use of a small buffer is sufficient to determine the volume of inspired or expired gas.

Each assistance apparatus 8 can also comprise an alert device 40 configured to produce an alert signal if the determined value of the at least one quality parameter is outside of a setpoint range, the setpoint range comprising expected values of the quality parameter, of which setpoint range at least one of the limits is determined according to the data that relate to the second emergency care procedure and that are received from the other assistance apparatus (e.g., another assistance apparatus 8). The production of an alert signal, if one of these parameters is outside of the setpoint range for this parameter, allows the rescuer to improve their chest compression maneuvers accordingly.

According to the disclosure, for a quality parameter of an emergency care procedure, at least one of the limits of the setpoint range can be determined as a function of data received from the assistance apparatus 8 for carrying out the other emergency care procedure.

Practice shows that, if active ventilations are carried out in parallel with the compressions, the pressure of the inspired gas in the lungs disturbs the performance of the compressions, has an impact on the measurement of the compressions and also has an impact on the measurement and the determination of the hemodynamic parameters. Thus, the performance of ventilation can result in the ventilation assistance apparatus 8 displaying unwanted alert signals that are likely to needlessly inconvenience the person performing the compressions. Similarly, practice shows that, if compressions are carried out in parallel with the ventilations, the intrathoracic pressures are such that it is very difficult to insufflate the expected volume of gas. Performing compressions in parallel with ventilation can then result in the compression assistance apparatus 8 displaying unwanted alert signals that are likely to needlessly inconvenience the person performing the ventilation.

Also, by determining at least one of the limits of the setpoint range for a quality parameter relating to an emergency care procedure as a function of data received from the assistance apparatus 8 for carrying out the other emergency care procedure, it is possible to avoid the displaying of unwanted alert signals.

According to one embodiment, in an assistance apparatus 8, the alert device 40 is configured to fix a limit, for example a lower limit, of the setpoint range for a quality parameter at a first value if the communication device 30 receives, from the assistance apparatus 8 for carrying out the second emergency care procedure, an information item of the type "other care procedure in progress," and otherwise at a second value. For example, in the compression assistance apparatus 8, the alert device 40 can be configured to fix a lower limit of the setpoint range for a parameter at a first value if the communication device 30 receives, from the ventilation assistance apparatus 8, an information item "ventilation in progress," and otherwise at a second value. In a numerical example, for the depth of the compressions, the lower limit (5 cm) of the ideal setpoint range (5 cm to 6 cm) can be lowered to 3 cm during the moments when ventilation is performed. Similarly, in the ventilation assistance apparatus 8, the alert device 40 can be configured to fix a lower limit of the setpoint range for a parameter at a first value if the communication device 30 receives, from the compression assistance apparatus 8, an information item "compression in progress," and otherwise at a second value. In a numerical example, for the inspired gas volume, the lower limit (400 ml) of the ideal setpoint range (400 ml to 600 ml) can be lowered to 300 ml during the moments when the compressions are performed.

In an assistance apparatus 8 according to the disclosure, the measuring device 10 can also comprise at least one sensor for measuring the variable representative of an expected effect of the care procedure, and a control circuit for the measurement sensor configured to calibrate the measurement sensor if the communication device 30 receives, from the assistance apparatus 8 for carrying out the other emergency care procedure, an information item of the type "no other care procedure in progress." The control circuit also controls the overall operation of the measurement sensor (or sensors) and, after calibration, it supplies a measured signal representing the change over time in the measured variable. The calibration makes it possible to determine at least one coefficient of the sensor by measuring the variable (pressure, acceleration, etc.) in the absence of another emergency care procedure in progress.

Practice shows that, when manual ventilation is in progress, it generates a positive pressure in the lungs, which causes lifting of the chest. Thus, if ventilation takes place during a calibration of the measurement sensor of a measuring device 10 of a compression assistance apparatus 8, the pressure of the inspired gas in the lungs and the resulting lifting of the chest come to distort the measurement of the initial value of the variable measured by the measuring device 10 of the compression assistance apparatus 8. Similarly, practice shows that, when compressions are in progress, the crushing of the chest and the resulting reduction in the pulmonary volume come to distort the measurement of the initial value of the variable measured by the measuring device 10 of the ventilation assistance apparatus 8.

Also, the fact that, in an assistance apparatus 8 according to the disclosure, the control circuit of the measuring device 10 is configured to calibrate the measurement sensor only if the communication device 30 receives from the ventilation assistance apparatus 8 an information item of the type "no other procedure in progress" makes it possible to carry out a more precise and more accurate calibration.

Each assistance apparatus 8 according to the disclosure can also comprise a display device 50 configured to display the determined value of the at least one quality parameter. Of course, the display device 50 can simultaneously display the determined value of several parameters, for example, for the quality of the compressions, the number of compressions already performed, the depth of the compressions and the frequency of the compressions, and, for the quality of the hemodynamics, the arterial pressure, the pulse wave speed, etc.

The display device 50 can also be configured to display the alert signal or the alert signals, when a quality parameter is outside of a setpoint range for this parameter. The display of at least one compression quality parameter and of a possible associated alert message allows the rescuer performing the compressions to quickly adjust their maneuvers in order to improve the quality of the compressions performed.

In a specific example of implementation, the display device 50 can comprise a small display screen such as an LCD screen, and the parameters can be displayed according to known graphic, visual and/or audio representations. For example, for each parameter, the numerical value of the parameter can be displayed, and the alert signal is, for example, displayed in the form of a light signal, for example a green signal if the value of the parameter is within the setpoint range, or a red signal if the value of the parameter is outside of the setpoint range, or, for example, a green signal if the value of the parameter is within the setpoint range, an orange signal if the parameter has a value close to the limits of the setpoint range, or a red signal if the value of the parameter is outside of the setpoint range. In another example, the numerical value of the parameter can be displayed in the form of a bar of which the height is a function of the numerical value to be displayed, and the alert signal is an audio signal of which the sound level is low when the value of the parameter is close to a limit and increases if the value of the parameter approaches the limit.

Also, in an assistance apparatus 8 according to the disclosure, the display device 50 can be configured to display instructions for carrying out an emergency care procedure, the instructions comprising, in particular, an expected value of the at least one quality parameter of the first emergency care procedure, the expected value being a function of the received data relating to the second emergency care procedure. This makes it possible to synchronize the actions of the rescuer who is performing the compressions with the actions of a rescuer who is performing ventilation actions in parallel or alternately, as will be seen better below.

Also in an assistance apparatus 8 according to the disclosure, the communication device 30 can be configured to receive from a user a choice of assistance protocol to be executed, the protocol comprising, in particular, the first emergency care procedure and the second emergency care procedure, and the display device 50 can be configured to display instructions suitable for execution of the first emergency care procedure, the instructions being a function of the received data relating to the second emergency care procedure.

As stated previously, an assistance system for cardiopulmonary resuscitation according to the disclosure comprises a compression assistance apparatus 8 and a ventilation assistance apparatus 8 as have been described above and as are claimed. The compression assistance apparatus 8 and the ventilation assistance apparatus 8 are intended to be used by at least two separate rescuers. According to the disclosure, the assistance system is characterized in that, in at least one of the assistance apparatuses 8, the data processing device is configured to process the at least one measured signal as a function of data received from the other of the assistance apparatuses 8.

The assistance system can be used according to the method described below, more particularly concerning assistance in executing a coordinated emergency care assistance protocol comprising at least the performance of a ventilation procedure and of a compression procedure. Of course, in addition and/or in parallel, each assistance apparatus 8 of the coordinated assistance system, that is to say the compression assistance apparatus 8 and the ventilation assistance apparatus 8, can execute the other functions for which it is configured (calibration of measurement sensors, measurement of a variable representative of a care procedure in progress, determination of the value of a quality parameter of the care procedure performed according to a first method or according to a second method, choice of limits of setpoint ranges for the quality parameters, production of alert signals, display of parameters and/or alert signals, etc.).

The method according to the disclosure for assistance in executing a coordinated assistance protocol comprises the following steps:

in at least one of the assistance apparatuses 8, the communication device 30 receives an assistance protocol from one of the rescuers and transmits the assistance protocol to the communication device 30 of the other of the assistance apparatuses 8, in the compression assistance apparatus 8, the display device 50 displays instructions for carrying out the compression procedure of the assistance protocol, the instructions depending on the compression procedure and depending on the data received from the ventilation assistance apparatus 8, and in the ventilation assistance apparatus 8, the display device 50 displays instructions for carrying out the ventilation procedure, the instructions depending on the ventilation procedure and depending on the data received from the compression assistance apparatus 8.

In addition to the ventilation and/or compression procedures to be performed, the assistance protocol received from one of the rescuers can comprise at least one patient parameter chosen from a set of parameters relating to the patient, comprising, in particular, a height, a weight, an age or a gender of the patient, and/or at least one therapeutic parameter chosen from a set of parameters relating to a therapeutic strategy, comprising, in particular, an invasive ventilation, a non-invasive ventilation, manual compressions, and mechanical compressions, the instructions for carrying out the compression procedure and/or the instructions for carrying out the ventilation procedure are also dependent on the at least one patient parameter and/or the at least one therapeutic parameter.

These parameters relating to the patient and/or relating to a therapeutic strategy make it possible to better adjust the setpoint ranges for the quality parameters, in particular the setpoint range for the volume of air to be insufflated or the setpoint range for the depth of the compressions.

According to one embodiment, suitable for executing an assistance protocol comprising the simultaneous performance of a ventilation procedure and of a compression procedure, the method comprises the following steps:

in the compression assistance apparatus 8:

the display device 50 displays a compression instruction comprising a compression frequency setpoint and a compression depth setpoint, the setpoints depending on the assistance protocol received, the measuring device 10 measures at least one variable representative of the compressions performed by one of the rescuers and produces a measured compression signal, from the measured compression signal, the signal-processing device 20 determines a number of compressions performed and produces a compression validation signal when the number of compressions performed reaches a predefined number, and when it receives the validation signal, the communication device 30 of the compression assistance apparatus 8 transmits a ventilation command to the communication device 30 of the ventilation assistance apparatus 8, and in the ventilation assistance apparatus 8, when the communication device 30 of the ventilation assistance apparatus 8 receives the ventilation command from the compression assistance apparatus 8:

the display device 50 displays a ventilation instruction comprising a ventilation frequency setpoint and a setpoint of the volume of gas to be insufflated, the setpoints being a function of the assistance protocol received.

These steps are, of course, repeated for as long as the ventilation and compression have to be carried out.

In parallel, in the compression assistance apparatus 8:

from the measured compression signal, the data processing device can determine a value of at least one quality parameter of the compressions, for example a compression frequency and/or a depth of the compressions, for example by choosing a determination method associated with presence of ventilation, and the alert device 40 can monitor the determined value of the parameters in relation to the expected value of the parameters and, if appropriate, can produce an alert, etc.

Similarly, in parallel, in the ventilation assistance apparatus 8:

from the measured ventilation signal, the data processing device can determine a value of at least one quality parameter of the ventilation, for example a ventilation frequency and/or a volume of pulsed air, for example by choosing a determination method associated with absence of compression, and the alert device 40 can monitor the determined value of the parameters in relation to the expected value of the parameters and, if appropriate, can produce an alert, etc.

According to another embodiment, suitable for executing an assistance protocol comprising the alternate performance of a compression procedure comprising a predefined number X of successive compressions and of a ventilation procedure comprising a predefined number Y of successive ventilations, the method comprising the following steps:

in the compression assistance apparatus 8, when the communication device 30 of the compression assistance apparatus 8 receives a compression command from the ventilation assistance apparatus 8:

the display device 50 displays a compression instruction comprising the number X of compressions to be carried out, a compression frequency setpoint and a compression depth setpoint, the setpoints being a function of the assistance protocol received, the measuring device 10 measures at least one variable representative of the compressions performed by one of the rescuers and produces a measured compression signal, from the measured compression signal, the signal-processing device 20 determines a number of compressions performed and produces a compression validation signal when the number of compressions performed reaches a predefined number, when it receives the compression validation signal, the display device 50 of the compression assistance apparatus 8 displays an instruction to stop the compressions, and when it receives the compression validation signal, the communication device 30 of the compression assistance apparatus 8 transmits a ventilation command to the communication device 30 of the ventilation assistance apparatus 8, and in the ventilation assistance apparatus 8, when the communication device 30 of the ventilation assistance apparatus 8 receives the ventilation command from the compression assistance apparatus 8:

the display device 50 displays a ventilation instruction comprising the number Y of ventilations to be carried out, a ventilation frequency setpoint and a setpoint of the gas volumes to be insufflated, the setpoints being a function of the protocol received, the measuring device 10 measures at least one variable representative of the ventilations performed by the other of the rescuers and produces a measured ventilation signal, from the measured ventilation signal, the signal-processing device 20 (20)-determines a number of ventilations performed and produces a ventilation validation signal when the number of ventilations performed reaches the number Y, when it receives the ventilation validation signal, the display device 50 displays an instruction to stop the ventilations, and when it receives the ventilation validation signal, the communication device 30 of the ventilation assistance apparatus 8 transmits a compression command to the communication device 30 of the compression assistance apparatus 8.

These steps are, of course, repeated for as long as the ventilation and compression have to be carried out.

Moreover, as before, in parallel, each assistance apparatus 8 can monitor the performance of a care procedure by determining a value of at least one quality parameter of the procedure in progress, by comparing the determined value to an expected value, and by producing an alert signal if necessary.

For the two method examples described above, variants may also be envisioned.

In the compression assistance apparatus 8:

The display device 50 can display an instruction to stop the compressions and can transmit a ventilation command, to the communication device 30 of the ventilation assistance apparatus 8, when the number of compressions performed reaches the number X or when the compressions have been stopped for more than N1 seconds.

The signal-processing device 20 can determine the number of compressions performed by counting the number of compressions detected in the measurement signal. In a variant, starting from the measured signal, the signal-processing device 20 can determine the depth of each compression performed and can determine the number of compressions performed by counting only the compressions for which the compression depth is greater than a minimum depth. In another variant, the signal-processing device 20 can determine the time that has elapsed since the start of the first compression and can determine the number of compressions performed by dividing the elapsed time by the compression frequency, for example by the frequency setpoint of the compression instruction.

Similarly, in the ventilation assistance apparatus 8:

The display device 50 can display an instruction to stop the ventilation and can transmit a compression command, to the communication device 30 of the compression assistance apparatus 8, when the number of ventilations performed reaches the number Y or when the ventilations have been stopped for more than N2 seconds.

The signal-processing device 20 can determine the number of ventilations performed by counting the number of ventilations detected in the measured signal. In a variant, starting from the measured signal, the signal-processing device 20 can determine the volume of gas insufflated at each ventilation performed and can determine the number of ventilations performed by counting only the ventilations for which the insufflated gas volume is greater than a minimum volume. In another variant, the signal-processing device 20 can determine the time that has elapsed since the start of the first ventilation, can determine the duration of a ventilation, for example of the first ventilation, and can determine the number of ventilations performed by dividing the elapsed time by the duration of a ventilation.

The invention claimed is:

1. An assistance apparatus for carrying out a first emergency care procedure, the assistance apparatus being configured to cooperate with a second assistance apparatus for carrying out a second emergency care procedure, the assistance apparatus comprising:

a measuring device configured to measure at least one variable representative of the first emergency care procedure carried out and to produce at least one measured signal;

a signal-processing device configured to determine, from the at least one measured signal, a value of at least one quality parameter of the first emergency care procedure carried out; and a communication device configured to receive, from the second assistance apparatus, data relating to the second emergency care procedure, the data comprising at least one item of information, a parameter, or an instruction, the signal-processing device further configured to process the at least one measured signal according to the received data relating to the second emergency care procedure, wherein the assistance apparatus is configured as a ventilation assistance apparatus, the first emergency care procedure comprising ventilation on a patient, the assistance apparatus being configured to cooperate with a ventilation mask coupled to a ventilation device for supplying respiratory gas, and wherein:

the at least one variable representative of the first emergency care procedure comprises a variable representative of the ventilation, the variable representative of the ventilation being chosen from a set of ventilation variables comprising a flow rate of inspired gas, a flow rate of expired gas, a pressure of the inspired gas, and a pressure of the expired gas; and the at least one quality parameter of the first emergency care procedure comprises at least one ventilation quality parameter, the at least one ventilation quality parameter being chosen from a set of ventilation parameters comprising a ventilation frequency, a volume of inspired air, a volume of expired air, a tidal volume or effective volume, a percentage of leaks, an insufflation pressure, an end-expiratory pressure, an insufflation time, and an expiration time.

2. The assistance apparatus of claim 1, wherein the signal-processing device is configured to determine the value of the at least one quality parameter according to a first determination method, if the communication device receives an information item, of the at least one item of information, of a type "other care procedure in progress" and, otherwise, according to a second determination method different from the first determination method.

3. The assistance apparatus of claim 2, wherein the first determination method and the second determination method each comprise an algorithm and an initial parameterization, and:

the algorithm of the second determination differs from the algorithm of the first determination method, or the initial parameterization of the second determination method differs from the initial parameterization of the first determination method.

4. The assistance apparatus of claim 1, further comprising an alert device configured to produce an alert signal if the determined value of the at least one quality parameter is outside a range of values, the range of values comprising expected values of the at least one quality parameter, and at least one limit of the range of values being determined as a function of the received data relating to the second emergency care procedure.

5. The assistance apparatus of claim 4, wherein the alert device is further configured to fix a lower limit, of the at least one limit of the range of values, for the at least one quality parameter at a first lower reference value if the communication device receives an information item, of the at least one item of information, of a type "other care procedure in progress" and, otherwise, at a second lower reference value different from the first lower reference value.

6. The assistance apparatus of claim 1, wherein the measuring device comprises at least one sensor for measuring the at least one variable representative of the first emergency care procedure, a control circuit of the at least one sensor being configured to calibrate the at least one sensor if the communication device receives an information item, of the at least one item of information, of a type "no other care procedure in progress.

7. The assistance apparatus of claim 1, further comprising a display device configured to display the determined value of the at least one quality parameter.

8. The assistance apparatus of claim 7, further comprising:

an alert device configured to produce an alert signal if the determined value of the at least one quality parameter is outside a range of values, the range of values comprising expected values of the at least one quality parameter, and at least one limit of the range of values being determined as a function of the received data relating to the second emergency care procedure, wherein the display device is further configured to display the alert signal.

9. The assistance apparatus of claim 7, wherein the display device is further configured to display instructions for carrying out the first emergency care procedure, the instructions comprising an expected value of the at least one quality parameter of the first emergency care procedure, the expected value depending on the received data relating to the second emergency care procedure.

10. The assistance apparatus of claim 7, wherein:

the communication device is further configured to receive from a user a choice of assistance protocol to be executed, the assistance protocol comprising the first emergency care procedure and the second emergency care procedure; and the display device is further configured to display instructions suitable for carrying out the first emergency care procedure, the instructions depending on the received data relating to the second emergency care procedure.

11. The assistance apparatus of claim 1, wherein:

the set of ventilation variables further comprises a variable representative of an oxygenation of the patient; and the set of ventilation parameters further comprises parameters relating to a quality of the patient's oxygenation, the parameters relating to the quality of the patient's oxygenation comprising a quantity of $CO_2$ present in the expired gas (EtCO2) and a quantity of oxygen in the patient's blood (SaO2).

12. An assistance system for cardiopulmonary resuscitation, comprising:

assistance apparatuses, comprising:

a compression assistance apparatus for carrying out compressions on a thoracic cage of a patient; and a ventilation assistance apparatus for carrying out ventilation on the patient, the compression assistance apparatus and the ventilation assistance apparatus being configured to be used by at least two separate rescuers, the compression assistance apparatus and the ventilation assistance apparatus configured to cooperate with one another, each of the assistance apparatuses comprising:

a measuring device configured to measure at least one variable representative of a first emergency care procedure, of the compressions and the ventilation, carried out and to produce at least one measured signal;

a signal-processing device configured to determine, from the at least one measured signal, a value of at least one quality parameter of the first emergency care procedure carried out; and a communication device configured to receive, from an other of the assistance apparatuses, data relating to a second emergency care procedure, of the compressions and the ventilation, the data comprising at least one item of information, a parameter, or an instruction, the signal-processing device further configured to process the at least one measured signal according to the received data relating to the second emergency care procedure received from the other of the assistance apparatuses.

13. A method for assistance in executing an assistance protocol comprising a ventilation procedure and a compression procedure, the method being implemented with aid of an assistance system as claimed in claim 12, the method comprising:

in one of the assistance apparatuses, the communication device receiving an assistance protocol from one of the rescuers and transmitting the assistance protocol to the communication device of the other of the assistance apparatuses;

in the compression assistance apparatus, a display device displaying instructions for carrying out the compression procedure of the assistance protocol, the instructions depending on the compression procedure and depending on the data received from the ventilation assistance apparatus; and in the ventilation assistance apparatus, an other display device displaying instructions for carrying out the ventilation procedure, the instructions depending on the ventilation procedure and depending on the data received from the compression assistance apparatus.

14. The method of claim 13, wherein:

the assistance protocol received from one of the rescuers also comprises both or either of:

at least one patient parameter chosen from a set of parameters relating to the patient, comprising a height, a weight, an age, and a gender, and at least one therapeutic parameter chosen from a set of parameters relating to a therapeutic strategy, comprising an invasive ventilation, a non-invasive ventilation, manual compressions, and mechanical compressions, the instructions for carrying out the compression procedure, the instructions for carrying out the ventilation procedure, or both are also dependent on at least one of:

the at least one patient parameter, and the at least one therapeutic parameter.

15. The method of claim 13, wherein, for simultaneous performance of the ventilation procedure and of the compression procedure, the method further comprises:

in the compression assistance apparatus:

the display device displaying a compression instruction, of the instructions for carrying out the compression procedure of the assistance protocol, the compression instruction comprising a compression frequency setpoint and a compression depth setpoint, the compression frequency setpoint and the compression depth setpoint depending on the assistance protocol received;

the measuring device measuring at least one variable representative of the compressions performed by one of the rescuers and producing a measured compression signal;

from the measured compression signal, the signal-processing device determining a number of the compressions performed and producing a compression validation signal when the number of the compressions performed reaches a predefined number; and when the compression assistance apparatus receives the compression validation signal, the communication device of the compression assistance apparatus transmitting a ventilation command to the communication device of the ventilation assistance apparatus; and in the ventilation assistance apparatus, when the communication device of the ventilation assistance apparatus receives the ventilation command from the compression assistance apparatus:

the other display device displaying a ventilation instruction, of the instructions for carrying out the ventilation procedure, the ventilation instruction comprising a ventilation frequency setpoint and a setpoint of a volume of gas to be insufflated, the ventilation frequency setpoint and the setpoint of the volume of gas to be insufflated being a function of the assistance protocol received.

16. The method of claim 13, wherein the assistance protocol comprises an alternate performance of the compression procedure and the ventilation procedure, the compression procedure comprising a predefined number X of successive compressions, of the compressions to be carried out on the thoracic cage of the patient, the ventilation procedure comprising a predefined number Y of successive ventilations, of the ventilations to be carried out on the patient, the method further comprising:

in the compression assistance apparatus, when the communication device of the compression assistance apparatus receives a compression command from the ventilation assistance apparatus:

the display device displaying a compression instruction, of the instructions for carrying out the compression procedure of the assistance protocol, the compression instruction comprising the predefined number X of successive compressions to be performed, a compression frequency setpoint, and a compression depth setpoint, the compression frequency setpoint and the compression depth setpoint being a function of the assistance protocol received;

the measuring device measuring at least one variable representative of the compressions performed by one of the rescuers and producing a measured compression signal;

from the measured compression signal, the signal-processing device determining a number of the compressions performed and producing a compression validation signal when the number of the compressions performed reaches a predefined number;

when the compression assistance apparatus receives the compression validation signal, the display device of the compression assistance apparatus displaying an instruction to stop the compressions; and when the compression assistance apparatus receives the compression validation signal, the communication device of the compression assistance apparatus transmitting a ventilation command to the communication device of the ventilation assistance apparatus; and in the ventilation assistance apparatus, when the communication device of the ventilation assistance apparatus receives the ventilation command from the compression assistance apparatus:

the other display device displaying a ventilation instruction, of the instructions for carrying out the ventilation procedure, the ventilation instruction comprising the predefined number Y of successive ventilations to be performed, a ventilation frequency setpoint and a setpoint of gas volumes to be insufflated, the ventilation frequency setpoint and the setpoint of the gas volumes to be insufflated being a function of the protocol received;

the measuring device measuring at least one variable representative of the ventilations performed by the other of the rescuers and producing a measured ventilation signal;

from the measured ventilation signal, the signal-processing device determining a number of the ventilations performed and producing a ventilation validation signal when the number of the ventilations performed reaches the predefined number Y;

when the ventilation assistance apparatus receives the ventilation validation signal, the other display device displaying an instruction to stop the ventilations; and when the ventilation assistance apparatus receives the ventilation validation signal, the communication device of the ventilation assistance apparatus transmitting a compression command to the communication device of the compression assistance apparatus.

* * * * *